(12) United States Patent
Cho et al.

(10) Patent No.: US 11,383,242 B2
(45) Date of Patent: Jul. 12, 2022

(54) CHANNEL STRUCTURE OF NUCLEIC ACID EXTRACTING CARTRIDGE

(71) Applicant: SD BIOSENSOR, INC., Suwon-si (KR)

(72) Inventors: Young Shik Cho, Yongin-si (KR); Hyo Guen Lee, Suwon-si (KR); Hae Joon Park, Seongnam-si (KR); Sun Young Lee, Suwon-si (KR); Kwan Hun Lim, Suwon-si (KR); In Ae Kim, Gwangmyeong-si (KR); Jae Young Kim, Suwon-si (KR); Hyo Lim Park, Suwon-si (KR); Dong Hun Kim, Suwon-si (KR)

( * ) Notice: Subject to any disclaimer, the term of this patent is extended or adjusted under 35 U.S.C. 154(b) by 73 days.

(21) Appl. No.: 16/956,588

(22) PCT Filed: Dec. 20, 2018

(86) PCT No.: PCT/KR2018/016307
§ 371 (c)(1),
(2) Date: Jun. 20, 2020

(87) PCT Pub. No.: WO2019/132405
PCT Pub. Date: Jul. 4, 2019

(65) Prior Publication Data
US 2021/0283596 A1    Sep. 16, 2021

(30) Foreign Application Priority Data

Dec. 28, 2017 (KR) .................. 10-2017-0182630

(51) Int. Cl.
*B01L 3/00* (2006.01)
*G01N 1/34* (2006.01)
*G01N 1/40* (2006.01)

(52) U.S. Cl.
CPC ............... *B01L 3/508* (2013.01); *G01N 1/34* (2013.01); *G01N 1/4044* (2013.01); *B01L 2300/123* (2013.01)

(58) Field of Classification Search
CPC ....... B01L 2300/123; B01L 2400/0478; B01L 2400/0644; B01L 3/502; B01L 3/502738;
(Continued)

(56) References Cited

U.S. PATENT DOCUMENTS

| 2005/0095172 A1 | 5/2005 | Nagaoka et al. | |
| 2006/0134397 A1* | 6/2006 | Smith | B01D 67/0093 428/304.4 |

(Continued)

FOREIGN PATENT DOCUMENTS

| EP | 2842628 | 3/2015 |
| JP | 2004504828 A | 2/2004 |

(Continued)

OTHER PUBLICATIONS

"Office Action for Japan Patent Application No. 2020-536255,dated Jun. 22, 2021."

(Continued)

*Primary Examiner* — Jennifer Wecker
*Assistant Examiner* — Jonathan Bortoli
(74) *Attorney, Agent, or Firm* — Harvest IP Law, LLP

(57) ABSTRACT

The present invention discloses a flow path structure of a cartridge for nucleic acid extraction comprising: a plurality of elongated grooves formed on the surface of the cartridge body; and a shaft hole formed in the center of the body, wherein the plurality of grooves have a starting point formed around the shaft hole and an ending point extending from the starting point toward the outer region of the body.

9 Claims, 3 Drawing Sheets

(58) Field of Classification Search
CPC ..... B01L 3/508; B01L 3/527; C12N 15/1003; G01N 1/34; G01N 1/4044; G01N 2035/00237; G01N 2035/00544; G01N 2035/0429; G01N 35/1009
See application file for complete search history.

(56) References Cited

U.S. PATENT DOCUMENTS

| | | | |
|---|---|---|---|
| 2011/0263461 A1* | 10/2011 | Kastury | ............... B01L 9/523 506/23 |
| 2014/0004505 A1 | 1/2014 | Su et al. | |
| 2015/0209789 A1* | 7/2015 | Kho | ............... C12Q 1/6806 435/287.2 |

FOREIGN PATENT DOCUMENTS

| | | | | |
|---|---|---|---|---|
| JP | 2005114414 A | | 4/2005 | |
| JP | 2016061610 A | * | 4/2016 | ............ G01N 35/08 |
| KR | 10-2007-0011525 | | 1/2007 | |
| KR | 10-2014-0046941 | | 4/2014 | |
| WO | 2014008381 | | 1/2014 | |
| WO | 2016117726 | | 7/2016 | |

OTHER PUBLICATIONS

"European Search Report for 18895731.0-1101/3734292 PCT/KR2018016307".

\* cited by examiner

[Fig. 1]
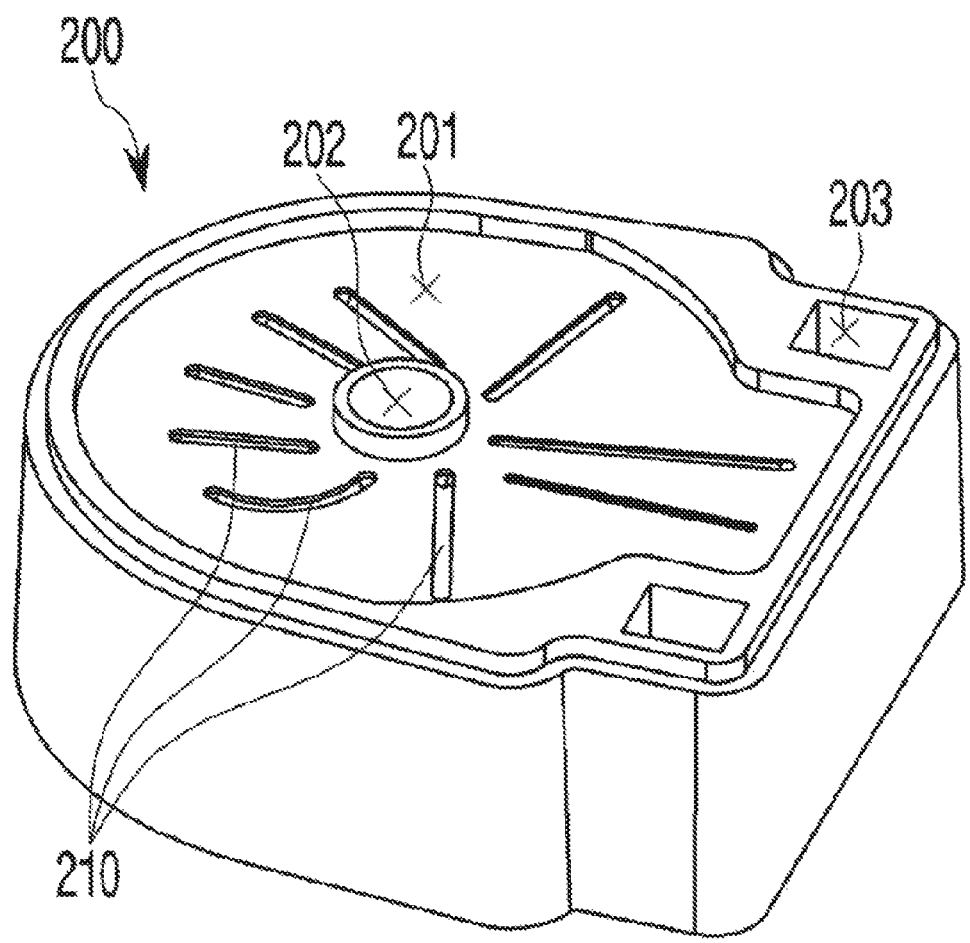

[Fig. 2]
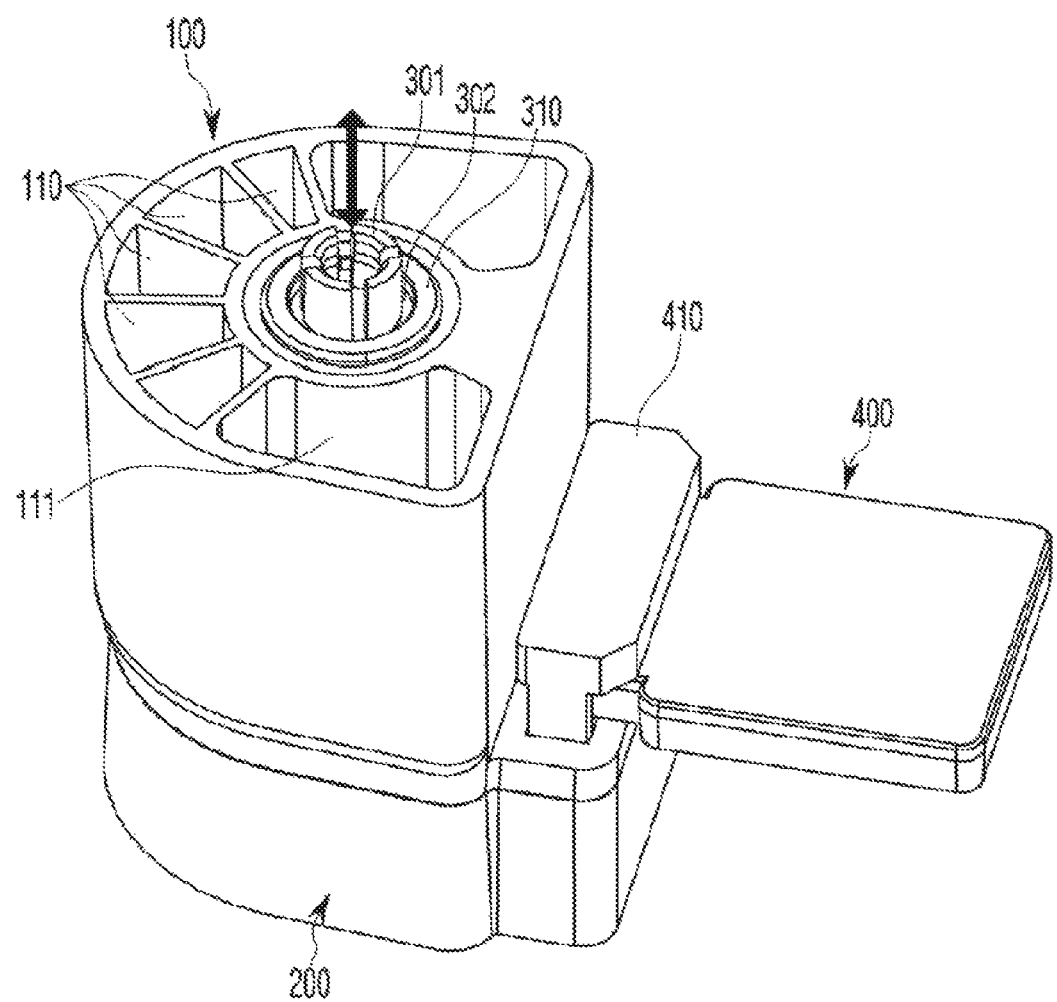

【Fig. 3】
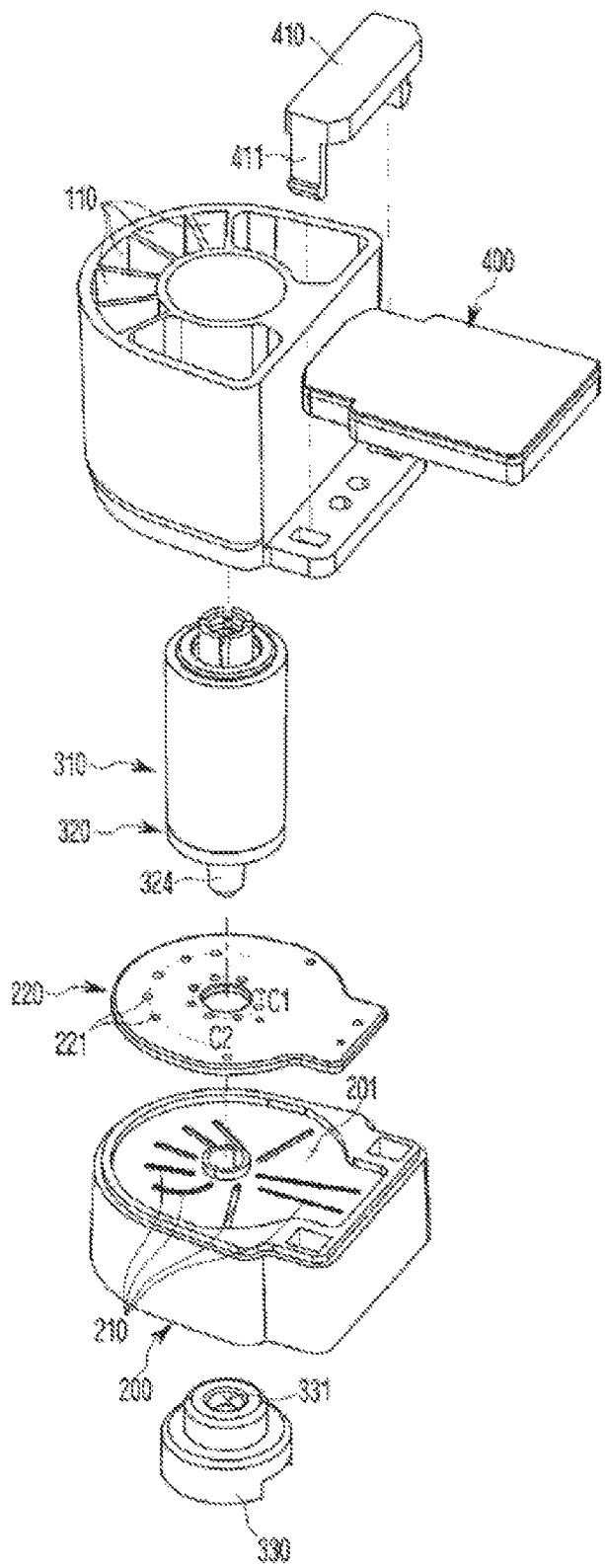

CHANNEL STRUCTURE OF NUCLEIC ACID EXTRACTING CARTRIDGE

TECHNICAL FIELD

The present invention relates to a flow path structure formed in a cartridge for nucleic acid extraction.

BACKGROUND ART

In modern times, it has become possible to interpret the cause of disease at the gene level with the development of biotechnology. As a result, the demand for manipulation and biochemical analysis of biological specimens to treat or prevent human diseases is increasing.

Also, in addition to the diagnosis of disease, the technology for extracting and analyzing nucleic acids from samples containing cells or biological specimens is required in various fields such as new drug development, preliminary examination of virus or bacterial infection, and forensic science.

Traditional nucleic acid extractors require each device for each processing process (concentration, purification) and require a long time to move to another device after one processing process is completed.

In the prior art (U.S. Pat. No. 6,374,684), in order to solve this problem, the piston head rotates in one cartridge, and a plurality of reagents can be sucked and mixed.

However, according to the prior art, a complex flow path structure must be implemented in a small piston head to process a plurality of reagents in one cartridge, so that the manufacturing cost of the cartridge can be increased and there is a problem that the entire cartridge may become unusable if a small error in the piston manufacturing process occurs.

Accordingly, research into a more intuitive and easy-to-implement flow path structure has been conducted to solve this problem.

DISCLOSURE

Technical Problem

An purpose of the present invention is to provide a flow path structure of a cartridge for nucleic acid extraction that makes it easier to suck and discharge samples and reagents.

Technical Solution

In order to achieve the above object, the flow path structure of the cartridge for nucleic acid extraction according to an embodiment of the present invention comprises a plurality of elongated grooves formed on the surface of the cartridge body and a shaft hole formed in the center of the body.

The plurality of grooves has a starting point formed around the shaft hole and an end point extending from the starting point toward the outer region of the body.

According to an embodiment of the present invention, the starting points of the plurality of grooves are arranged at the same distance from the shaft hole.

According to an embodiment of the present invention, the starting points of the plurality of grooves are disposed at the same angle from each other.

According to an embodiment of the present invention, the starting points of the plurality of grooves are disposed 45 degrees apart from other neighboring starting points, respectively.

According to an embodiment of the present invention, further provided with an additional groove having a different starting point spaced apart from the shaft hole.

According to an embodiment of the present invention, the end points of five adjacent grooves among the plurality of grooves are arranged at the same distance from the shaft hole.

According to an embodiment of the present invention, it further includes a rubber pad covering the surface.

According to an embodiment of the present invention, the rubber pad is provided with through holes overlapping the start and end points of the grooves.

According to one embodiment of the present invention, the surface includes an outer wall surrounding the rubber pad.

According to one embodiment of the invention, the outer wall is formed to have the same height as the thickness of the rubber pad.

Effects of the Invention

According to the flow path structure of the cartridge for nucleic acid extraction according to an embodiment of the present invention, a flow path for sucking and discharging samples and reagents is formed in the cartridge body to distinguish a space in which reagents are mixed and a space for movement. This simplifies the structure of the piston and improves the performance of the cartridge.

DESCRIPTION OF DRAWINGS

FIG. 1 is a conceptual diagram for explaining the flow path structure of a cartridge for nucleic acid extraction according to an embodiment of the present invention.

FIG. 2 is a perspective view of a cartridge for nucleic acid extraction apparatus according to an embodiment of the present invention.

FIG. 3 is an exploded view of the cartridge for nucleic acid extraction apparatus according to an embodiment of the present invention.

MODE FOR INVENTION

Hereinafter, the present invention will be described in more detail with reference to the drawings. In this specification, the same or similar reference numerals are assigned to the same or similar configurations in different embodiments, and the description is replaced with the first description. As used herein, a singular expression includes a plural expression unless the context clearly indicates otherwise. In addition, the suffixes "module" and "region" for components used in the following description are given or mixed only considering the ease of writing the specification, and do not have meanings or roles that are distinguished from each other.

FIG. 1 is a conceptual diagram for explaining a flow path structure of a cartridge for nucleic acid extraction according to an embodiment of the present invention.

Referring to FIG. 1, a plurality of grooves (210) extending long may be formed on the surface of the cartridge body (200). The plurality of grooves (210) form a flow path through which samples and reagents move.

A shaft hole (202) may be formed in the center of the body, and a shaft (324) of the piston may be inserted into the shaft hole (202).

The plurality of grooves (210) may be formed to start at the center of the cartridge body (200) and end at the outer region. In other words, the plurality of grooves (210) has a starting point formed around the shaft hole (202) and an end point extending from the starting point toward the outer region of the body.

As shown, the starting points of the plurality of grooves (210) may be arranged at the same distance from the shaft hole (202). That is, the starting points can be placed on a circumference that is the same distance from the center of the shaft hole (202). According to this structure, as the piston rotates, the liquid port formed on the lower body of the piston may overlap the starting point of each flow path.

The starting point of each flow path may be arranged at a certain angle from each other. In other words, the starting points of the plurality of grooves may be arranged at the same angle as the starting points of other grooves adjacent to each other.

For example, according to an embodiment of the present invention, eight flow paths may be formed in the cartridge body, and the starting points of the respective flow path may be arranged at the same angle from each other. That is, the starting point of each flow path may be arranged 45 degrees apart from other neighboring starting points.

According to an embodiment of the present invention, the eight flow paths may be composed of a sample flow path (213), a reagent flow path (211a, 211b, 211c, 211d, 211e, 212), and an amplification module flow path (215).

According to another embodiment of the present invention, an additional flow path (214) may be formed in the cartridge body in addition to the flow paths. The distance from the center of the shaft hole (202) to the starting point of the additional flow path (214) may be formed differently from the distance to the starting point of other flow paths.

When the piston rotates, the liquid port formed on the lower body of the piston overlaps the starting points of the other flow path but does not overlap the starting points of the additional flow path (214). That is, the additional flow path (214) may be used for different purposes from other flow paths. According to an embodiment of the present invention, an additional flow path may be used as a flow path for controlling vacuum when nucleic acids are injected into the amplification module.

As shown, the end points of the five grooves (211a, 211b, 211c, 211d, 211e) constituting the reagent flow path among the plurality of grooves may be disposed on the same circumference.

Hereinafter, how the flow path structure described above is implemented in the cartridge will be described in detail with reference to FIGS. 2 to 3.

FIG. 2 is a perspective view of the cartridge, FIG. 3 is an exploded view of the cartridge shown in FIG. 2.

Referring to FIGS. 2 to 3, the cartridge for nucleic acid extraction may largely be comprised a first body (100), a second body (200), a piston (300), a nucleic acid amplification module (400), and the like.

The first body (100) may be used to store a plurality of reagents.

According to the illustrated, the first body (100) may be formed of a plurality of chambers (110) forming a compartment separated from each other. Different reagents or samples are disposed in each chamber (110) and each chamber (110) forms an independent space so that the reagents do not mix with each other.

The second body (200) guides a path through which the reagent or sample stored in the first body (100) moves.

According to an embodiment of the present invention, the second body (200) may have a liquid flow path through which liquid can move and an air flow path through which air can move, and In order to prevent leakage of the liquid when combined with the first body (100), it may include a pad (220) disposed on the upper surface. When the pad (220) and the cartridge second body (200) are combined, the liquid flow path and the air flow path of the cartridge second body (200) are blocked by the pad (220) to form a space so that the perfect flow path (210) is completed.

The liquid flow path is connected to the rubber pad (220) and the first body (100) to provide a space for samples and reagents to move and mix.

The air flow path connects the amplification module and the vacuum control region of the piston (300) to control the vacuum that can occur when the nucleic acid extracted by the amplification module moves, and serves to prevent contamination of the amplification products that may occur during nucleic acid amplification.

The pad (220) has a plurality of liquid port connection holes, through which the liquid and air flow paths at the bottom of the cartridge are connected to the plurality of reagent chambers (110) located in the cartridge first body (100). The center upper surface of the rubber pad (220) is combined with the bottom surface of the piston lower body (320), and the filter port and the liquid port of the piston lower body (320) rotate while being located in parallel with the liquid port located in the center of the rubber pad (220) and serves to prevent liquid leakage that may occur during liquid movement and mixing.

More specifically, a plurality of flow paths (210) may be formed on the upper region of the second body (200). Each flow path (210) does not cross each other and is formed to extend from the center of the second body (200) to the outer region. As illustrated, some flow paths (210) may have one end disposed on the same circumference and the other end also disposed on the same circumference.

The pad (220) may be combined to the upper region of the second body (200).

The upper region of the second body (200) may be formed with a recessing region (201) recessed toward the bottom, and the pad (220) may be engaged with the recessing region (201) on the upper region of the second body (200).

In other words, an outer wall surrounding the pad may be formed on the upper surface of the second body (200), and the outer wall may be formed to have the same height as the thickness of the pad.

As the pad (220) is in close contact with the upper surface of the second body (200), the flow paths (210) may be sealed. The pad (220) may be formed of rubber or synthetic resin having elasticity so that the pad (220) may be more closely adhered to the second body (200).

A plurality of holes penetrating the pad (220) up and down may be formed in the pad (220).

According to an embodiment of the present invention, the holes are arranged to overlap the top and bottom of ends of the flow paths (210). In other words, holes formed in the pad (220) may be paired in pairs to be connected through the flow path (210).

The pad (220) may comprise a plurality of holes disposed on the same circumference (C1) in the center and a plurality of holes disposed on the same circumference (C2) in the outer region.

The piston (300) may comprise a piston upper body (310) and a piston lower body (320).

In the upper body (310) of the piston (300), an inner space in which reagents and samples can be mixed is formed, and a control rod module of the piston (300) moving up and down may be disposed in the inner space.

The piston control rod module may include a coupling region (301) coupled with a driving region of the nucleic acid extraction device and a sealing region (302) moving up and down in close contact with the piston inner space.

The piston lower body (320) is combined with the piston upper body (310) to form one body.

The piston lower body (320) may be combined with the rotation control module (330).

According to the illustrated, the piston upper body (310) is inserted into the hole formed in the central region of the first body (100) and the shaft (324) of the piston lower body (320) is inserted into the hole formed in the central region of the second body (200).

The shaft (324) of the piston lower body (320) is fixed in engagement with the rotation control module (330) combined to the bottom of the second body (200).

The nucleic acid amplification module (400) may be combined with the first body (100) or the second body (200)

The internal flow path (210) may be formed inside the nucleic acid amplification module (400), and one end of the internal flow path (210) may be formed to overlap with at least one of the flow paths (210) formed in the second body (200).

According to one embodiment of the present invention, there may be a fixing member (410) for covering the nucleic acid amplification module (400) and coupling the first body (100) and the second body (200) so that the nucleic acid amplification module (400) is not arbitrarily separated.

According to the flow path structure of the cartridge for nucleic acid extraction described above, a flow path for sucking and discharging samples and reagents is formed in the cartridge body to distinguish a space in which reagents are mixed and a space for movement. This simplifies the structure of the piston and improves the performance of the cartridge.

The flow path structure of the cartridge for nucleic acid extraction described above is not limited to the configuration and method of the above-described embodiments, but the above embodiments are selectively combined with all or part of each embodiment so that various modifications can be made. It may be configured.

The invention claimed is:

1. A flow path structure of a cartridge for nucleic acid extraction, wherein the cartridge comprises:
   a first body having a hole formed in a central region of the first body and containing a plurality of chambers for storing one or more reagents or samples;
   a second body, coupled to the lower portion of the first body, having a surface formed with a plurality of grooves;
   a piston having an upper body and a lower body joined to the upper body in an integrated manner, wherein the upper body is configured to provide an inner space in which one or more reagents and one or more samples are mixed together, and wherein the lower body includes a port configured to overlap any one of the plurality of grooves when the piston rotates;
   a rotation control module coupled to the lower body of the piston;
   a piston control rod module configured to move up and down in close contact with the piston inner space; and
   a pad, disposed between the first body and the upper surface of the second body, formed with a first group of holes arranged at a first circumference of a center of the pad and a second group of holes arranged at a second circumference of the center,
   wherein a radius of the first circumference is different from a radius of the second circumference and any one of the first group of holes are configured to overlap the port of the rotating piston, each hole of the groups having a sufficient length to penetrate the pad, and
   wherein the plurality of grooves are configured to form a plurality of respective flow paths connecting a pair of the holes in the pad.

2. The flow path structure of a cartridge for nucleic acid extraction according to claim 1, wherein a shaft hole, into which a shaft of the piston is inserted, is formed in a center of the second body and wherein starting points of the plurality of grooves are arranged at a same distance from the shaft hole.

3. The flow path structure of a cartridge for nucleic acid extraction according to claim 2, wherein said starting points of the plurality of grooves are disposed at the same angle to each other.

4. The flow path structure of a cartridge for nucleic acid extraction according to claim 2, wherein the starting points of the plurality of grooves are disposed at 45 degrees between neighboring starting points along the circumferential direction.

5. The flow path structure of a cartridge for nucleic acid extraction according to claim 4, further comprising an additional groove having a different starting point spaced apart from the shaft hole along the circumferential direction.

6. The flow path structure of a cartridge for nucleic acid extraction according to claim 4, wherein end points of five adjacent grooves among the plurality of grooves are arranged at the same distance from the shaft hole.

7. The flow path structure of a cartridge for nucleic acid extraction according to any one of claims 1 to 6, wherein said pad is a rubber pad.

8. The flow path structure of a cartridge for nucleic acid extraction according to claim 7, wherein an upper portion of the said surface of the second body comprises an outer wall surrounding the rubber pad.

9. The flow path structure of a cartridge for nucleic acid extraction according to claim 8, wherein the outer wall is formed to have a same height as a thickness of the rubber pad.

* * * * *